(12) United States Patent
Haines et al.

(10) Patent No.: US 9,936,946 B2
(45) Date of Patent: Apr. 10, 2018

(54) SUTURE PASSER AND METHOD OF OPERATING SAME

(71) Applicant: Cook Medical Technologies LLC, Bloomington, IN (US)

(72) Inventors: Joshua Haines, West Chester, OH (US); Amro Kamel, Bloomington, IN (US); Brian Feng, Bloomington, IN (US); Jeff Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 709 days.

(21) Appl. No.: 14/315,707

(22) Filed: Jun. 26, 2014

(65) Prior Publication Data

US 2015/0018854 A1 Jan. 15, 2015

Related U.S. Application Data

(60) Provisional application No. 61/846,106, filed on Jul. 15, 2013.

(51) Int. Cl.
*A61B 17/04* (2006.01)
*A61B 17/00* (2006.01)
*A61B 17/06* (2006.01)

(52) U.S. Cl.
CPC ...... *A61B 17/0483* (2013.01); *A61B 17/0469* (2013.01); *A61B 17/0485* (2013.01); *A61B 2017/00349* (2013.01); *A61B 2017/06019* (2013.01); *A61B 2017/06042* (2013.01)

(58) Field of Classification Search
CPC ............ A61B 17/0483; A61B 17/0485; A61B 2017/06042; A61B 2017/06019; A61B 17/0469; A61B 17/00349
See application file for complete search history.

(56) References Cited

U.S. PATENT DOCUMENTS 683,655 A * 10/1901 Mersch ................. D05B 81/00
 223/104
722,105 A * 3/1903 Hervey ................. D05B 81/00
 223/104
790,120 A * 5/1905 Garrett ................. D05B 85/00
 223/102

(Continued)

FOREIGN PATENT DOCUMENTS

WO 2004002324 1/2004
WO 2006023975 3/2006

*Primary Examiner* — Jing Ou
(74) *Attorney, Agent, or Firm* — Liell & McNeil

(57) ABSTRACT

A suture passer includes a stylet and a cannula having an open distal end defining a cannula outer diameter. The stylet has a proximal segment configured for receipt within the cannula and including a suture retention notch, and a distal segment having an expanded outer diameter substantially matching the cannula outer diameter. The distal segment of the stylet terminates at a distal cutting edge. The suture passer includes a retracted position in which the proximal segment of the stylet is received within the cannula through the open distal end and a shoulder defining a transition between the proximal segment and the distal segment abuts the open distal end of the cannula, and an extended position in which the suture retention notch is distally disposed relative to the open distal end of the cannula.

19 Claims, 4 Drawing Sheets

(56) References Cited

U.S. PATENT DOCUMENTS

| | | | | |
|---|---|---|---|---|
| 1,118,190 | A | * | 11/1914 | Eagleston .............. D05B 81/00 223/104 |
| 1,539,221 | A | * | 5/1925 | Tennant ................. B23K 9/282 219/143 |
| 1,580,859 | A | * | 4/1926 | Schulze ................. D05B 85/02 223/102 |
| 1,867,624 | A | * | 7/1932 | Hoffman ............ A61B 10/0266 600/567 |
| 1,998,418 | A | * | 4/1935 | Fridolph ................ D05C 15/20 223/102 |
| 4,441,497 | A | | 4/1984 | Paudler |
| 5,281,237 | A | * | 1/1994 | Gimpelson ........ A61B 17/0469 606/139 |
| 5,312,422 | A | | 5/1994 | Trott |
| 5,364,410 | A | * | 11/1994 | Failla ................. A61B 17/0469 606/135 |
| 5,387,227 | A | * | 2/1995 | Grice ................. A61B 17/0469 128/898 |
| 5,433,722 | A | * | 7/1995 | Sharpe ............... A61B 17/0469 606/139 |
| 5,439,467 | A | | 8/1995 | Benderev et al. |
| 5,462,562 | A | | 10/1995 | Elkus |
| 5,474,565 | A | | 12/1995 | Trott |
| 5,618,290 | A | | 4/1997 | Toy et al. |
| 5,741,278 | A | * | 4/1998 | Stevens ........... A61B 17/12013 606/139 |
| 5,746,752 | A | | 5/1998 | Burkhart |
| 6,547,807 | B2 | | 4/2003 | Chan et al. |
| 6,638,283 | B2 | | 10/2003 | Thal |
| 6,723,107 | B1 | | 4/2004 | Skiba et al. |
| 8,292,903 | B2 | | 10/2012 | Dreyfus et al. |
| 2002/0147456 | A1 | * | 10/2002 | Diduch .............. A61B 17/0469 606/144 |
| 2003/0036767 | A1 | * | 2/2003 | Chang .............. A61B 17/06109 606/148 |
| 2012/0143220 | A1 | | 6/2012 | Morgan et al. |
| 2012/0283753 | A1 | | 11/2012 | Saliman et al. |
| 2013/0030450 | A1 | | 1/2013 | Dreyfuss et al. |

* cited by examiner

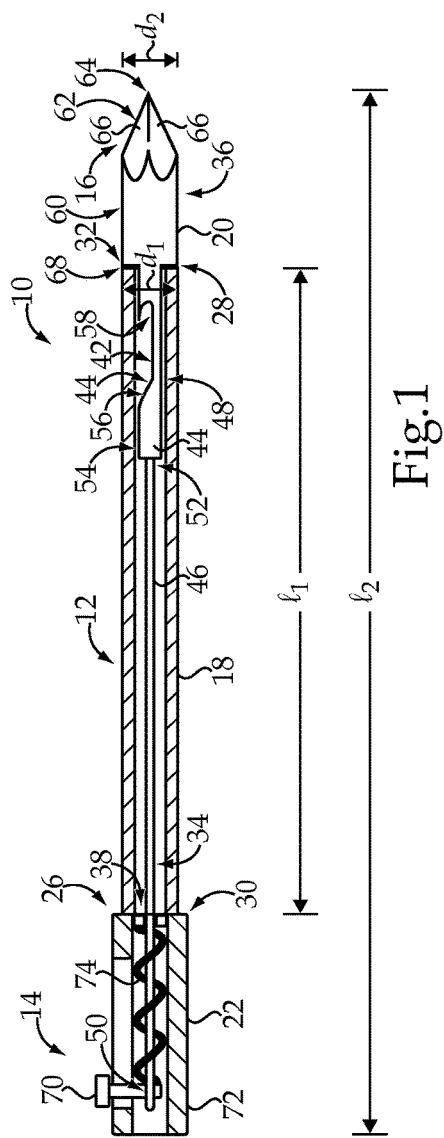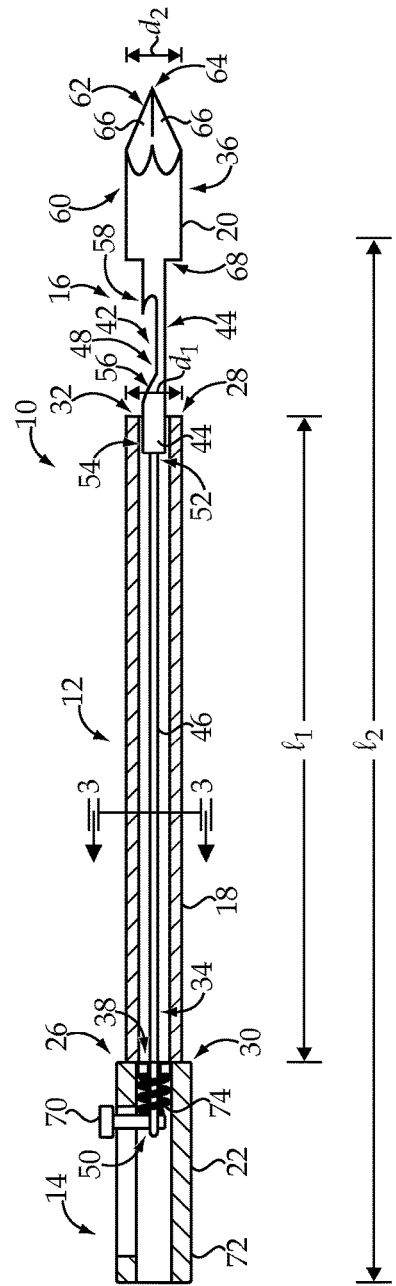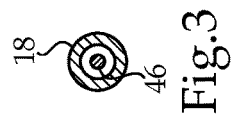

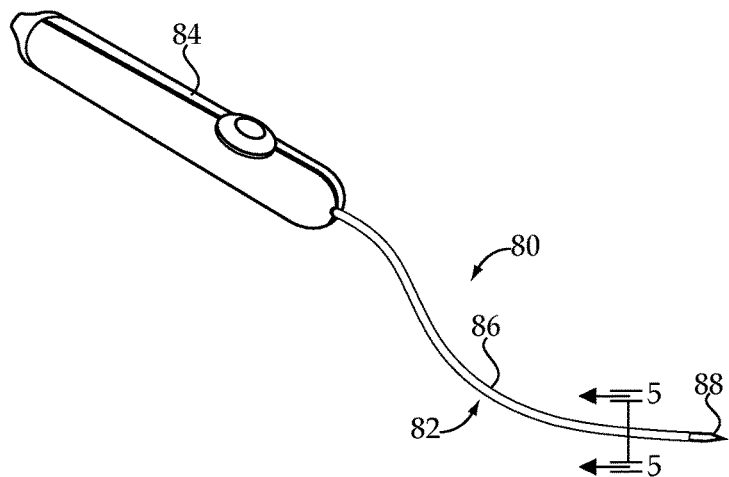
Fig.4  Fig.5
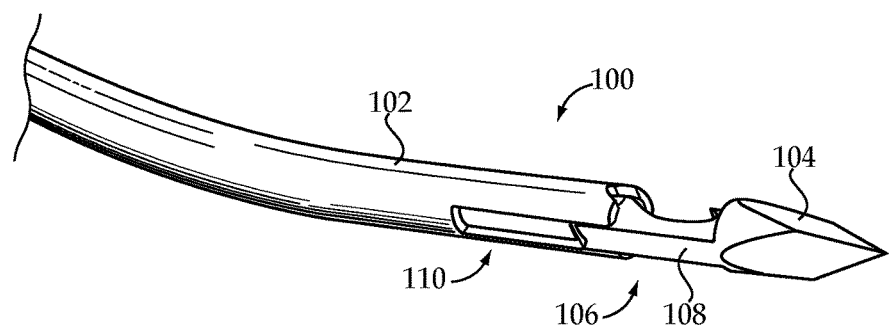
Fig.6
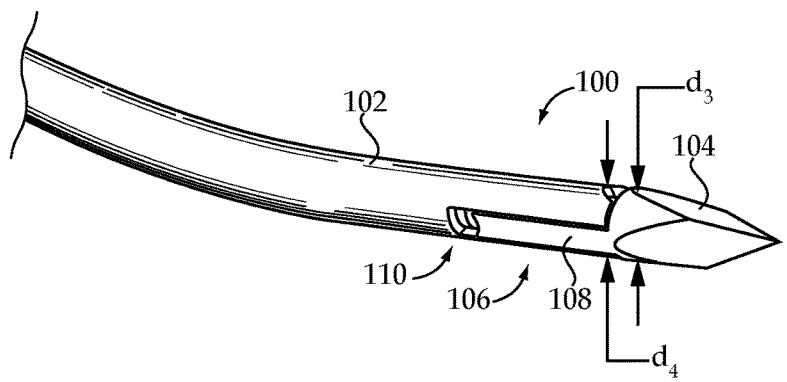
Fig.7

SUTURE PASSER AND METHOD OF OPERATING SAME

TECHNICAL FIELD

The present disclosure relates generally to a suture passer including a cannula and a stylet, and more particularly to a suture passer having a retracted position providing a continuous outer diameter at a transition between the cannula and the stylet.

BACKGROUND

A suture passer is a device used by a clinician to pass sutures through soft tissue. For example, the suture passer may be capable of capturing a suture and either pushing or pulling the suture through the soft tissue. Suture passers may be used in a variety of procedures, including a ventral hernia repair. Ventral hernia repairs typically involve the placement of a soft tissue repair prosthetic across an abdominal wall defect. During a minimally invasive procedure, such as a laparoscopic procedure, the prosthetic may be delivered into the abdominal cavity and positioned over the abdominal wall defect. Sutures may be applied through the prosthetic and all or a portion of the abdominal wall to secure positioning of the prosthetic. A suture passer may be used to pass one or more of the sutures through the skin, fascia, and muscle of the abdominal wall during attachment of the prosthetic.

U.S. Pat. No. 5,439,467 to Benderev et al. teaches a suture passer having an elongate probe axially movably disposed within a tubular probe guide between a retracted position and an extended position in which a sharpened distal tip of the elongate probe is exposed. The elongate probe has a recess, which cooperates with an opening through the tubular probe guide for receiving a suture. The suture passer taught by benderev et al., and other available suture passers, may suffer from drawbacks, including difficulty passing the suture passer smoothly and efficiently through the abdominal wall. For this reason, and others, there is a continuing need for improved suture passer devices.

The present disclosure is directed toward one or more of the problems or issues set forth above.

SUMMARY OF THE DISCLOSURE

In one aspect, a suture passer includes a stylet and a cannula having an open distal end defining a cannula outer diameter. The stylet has a proximal segment configured for receipt within the cannula and including a suture retention notch, and a distal segment having an expanded outer diameter substantially matching the cannula outer diameter. The distal segment of the stylet terminates at a distal cutting edge. The suture passer includes a retracted position in which the proximal segment of the stylet is received within the cannula through the open distal end and a shoulder defining a transition between the proximal segment and the distal segment abuts the open distal end of the cannula, and an extended position in which the suture retention notch is distally disposed relative to the open distal end of the cannula.

In another aspect, a method of operating a suture passer is provided. The suture passer includes a cannula having an open distal end defining a cannula outer diameter. The suture passer also includes a stylet having a proximal segment configured for receipt within the cannula and including a suture retention notch, and a distal segment having an expanded outer diameter substantially matching the cannula outer diameter. The distal segment of the stylet terminates at a distal cutting edge. The method includes a step of advancing the suture passer through soft tissue with the suture passer in a retracted position defining a continuous outer diameter at a transition between the cannula and the stylet. In the retracted position, the proximal segment of the stylet is received within the cannula through the open distal end and a shoulder defining a transition between the proximal segment and the distal segment abuts the open distal end of the cannula. The method also includes moving the suture passer from the retracted position to an extended position in which the suture retention notch is distally disposed relative to the open distal end of the cannula. A suture is received within the suture retention notch of the stylet and captured with the suture passer by returning the suture passer to the refracted position.

BRIEF DESCRIPTION OF THE DRAWINGS

FIG. 1 is a partially sectioned side diagrammatic view of a suture passer, shown in a retracted position, according to one embodiment of the present disclosure;

FIG. 2 is a partially sectioned side diagrammatic view of the suture passer of FIG. 1, shown in an extended position;

FIG. 3 is a cross sectional view taken along lines 3-3 of FIG. 2;

FIG. 4 is a perspective view of a suture passer including a cannula having a preformed curve, according to another embodiment of the present disclosure;

FIG. 5 is a cross sectional view taken along lines 5-5 of FIG. 4;

FIG. 6 is a perspective view of a distal portion of another exemplary suture passer, according to the present disclosure, shown in an extended position;

FIG. 7 is a perspective view of the distal portion of the suture passer of FIG. 6, shown in a retracted position;

DETAILED DESCRIPTION

Figure 8:
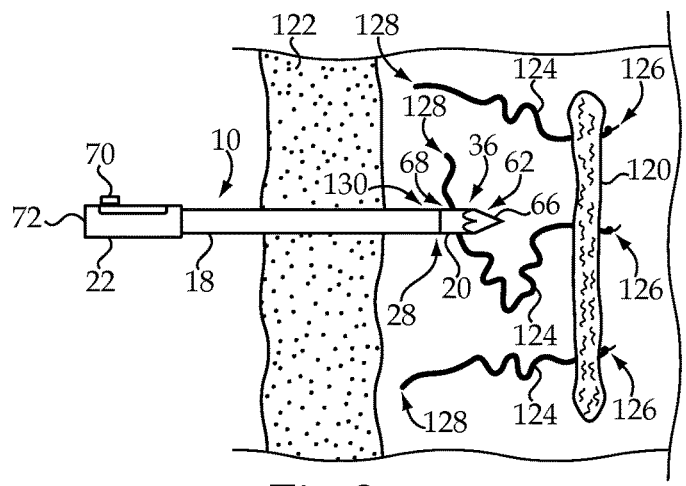
FIG. 8 is a partially sectioned side diagrammatic view of soft tissue of a patient depicting one stage of a treatment procedure using the suture passer of FIG. 1.

Referring to FIG. 1, there is shown a suture passer 10 according to one embodiment of the present disclosure. The suture passer 10 has an elongate body 12 having a proximal end 14 and a distal end 16, and generally includes a cannula 18 and a stylet 20. A handle 22 may be disposed at the proximal end 14 of the suture passer 10 and may be configured for moving one of the cannula 18 and the stylet 20 relative to another of the cannula 18 and the stylet 20. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The cannula 18 includes a tubular body 24 extending from an open proximal end 26 to an open distal end 28. The open proximal end 26 may define a blunt end 30 of the cannula 18 and may be attached to the handle 22, which will be discussed in greater detail below. The open distal end 28 may also define a blunt end 32 of the cannula 18 and defines a cannula outer diameter $d_1$. The cannula 18 may be made from any of a number of materials, including any of a variety of common biocompatible medical tube materials, such as a stainless steel, or other metal, or a vinyl, plastic, rubber, or silicone, to name a few. Although the material selection may depend on the intended use of the suture passer 10, the material or materials for the cannula 18 may be selected to provide a sufficient amount of stiffness, such as to provide precise placement of the suture passer 10 when passed through soft tissue.

The stylet 20 includes a proximal segment 34 and a distal segment 36. The proximal segment 34 is configured for receipt within the cannula 18 and may span a majority of a length $l_1$ of the cannula 18, which may define a majority of a length $l_2$ of the suture passer 10. The proximal segment 34 of the stylet 20 may have a proximal end 38 attached to the handle 22 and includes a suture retention notch 40 positioned at a distal end 42 of the proximal segment 34. As shown, the proximal segment 34 may include a body portion 44 and a wire portion 46, also referred to as a control wire. In particular, the proximal segment 34 may include the control wire 46 and a proximal length 48 of the body portion 44, both of which may be received within the cannula 18. According to the depicted embodiment, a proximal end 50 of the control wire 46, which corresponds to the proximal end 38 of the proximal segment 34, may be attached to the handle 22, while a distal end 52 of the control wire 46 may be attached to a proximal end 54 of the body portion 44.

The suture retention notch 40 may be receded relative to an external surface of the stylet 20. In particular, the suture retention notch 40 may be receded from a surface of the proximal length 48 of the body portion 44, which may be received within the cannula 18. The suture retention notch 40 may have any of a variety of shapes and/or configurations and, as shown, may be oriented along a longitudinal axis of the stylet 20. According to the exemplary embodiment, the suture retention notch 40 may extend distally from and may include a proximal slope 56. A distal hook 58 may also be provided to assist in capturing a suture, as will be described below. As should be appreciated, the length, width, and shape of the suture retention notch 40 may vary greatly from the depiction provided and still be suitable for capturing a suture, as described herein.

The distal segment 36 of the stylet 20, which represents a portion of the stylet 20 that will not be received within the cannula 18, has an expanded outer diameter $d_2$ substantially matching the cannula outer diameter $d_1$. In particular, the distal segment 36 of the stylet 20 may include a distal length 60 of the body portion 44, introduced above, having the expanded outer diameter $d_2$. The body portion 44 may be substantially solid, with the exception of the suture retention notch 40, and may terminate distally at a distal cutting edge 62. That is, the distal segment 36 of the stylet 20 may have the expanded outer diameter $d_2$ and may terminate at a tip or point 64 configured to pierce soft tissue, as will be described below. For example, the distal segment 36 may terminate at a tip having a multitude of bevels 66, as shown. According to some embodiments, two to five bevels may be preferred, and according to a specific embodiment, a three-sided beveled tip may be used.

The stylet 20 may be defined by one unitary component or a plurality of components configured to move together. For example, the proximal segment 34 of the stylet 20, which is the portion configured for receipt within the cannula 18, may have a consistent cross sectional shape and size along its length, with the exception of the suture retention notch 40. For example, the entire proximal segment 34 may have a shape and size consistent with the proximal length 48 of the depicted body portion 44. According to some embodiments, the proximal length 48 of the body portion 44 may have an outer surface that slides smoothly relative to an inner surface of the cannula 18, while retaining a close fit.

Alternatively, for example, the proximal segment 34 may include the control wire 46, which may have an ovoid cross-sectional shape as shown in FIG. 3, and the proximal length 48 of the body portion 44 as separate components that are attached together chemically, mechanically, or otherwise. For example, the control wire 46, which may have a smaller diameter than the proximal length 48 of the body portion 44, may be attached to the body portion 44 using adhesives, welding, fasteners, or the like. As shown, the proximal length 48 of the body portion 44 may have a length sufficient to support the suture retention notch 40, while the control wire 46 defines the remaining portion of the proximal segment 34.

Yet alternatively, the wire portion 46 and the body portion 44 may be one unitary component that is machined to form the depicted shape, or a suitable alternative. For example, a piece of round metal bar may be turned down on a lathe to fit an inner diameter of the cannula 18. The suture retention notch 40 and reduced diameter wire portion 46 may then be cut using electrical discharge machining, for example. Finally, a grinding machine may be used to form the bevels 66. As should be appreciated, the stylet 20 disclosed herein may be formed in any of a number of ways, which may be selected based on manufacturing preferences, costs, performance, etc.

The handle 22 may be configured to move the suture passer 10 between a retracted position, as shown in FIG. 1, and an extended position, as shown in FIG. 2. According to the retracted position of FIG. 1, the proximal segment 34 of the stylet 20 may be received within the cannula 18 through the open distal end 28 and a shoulder 68 defining a transition between the proximal segment 34 and the distal segment 36 abuts the open distal end 28 of the cannula 18. According to the extended position of FIG. 2, the stylet 20 and/or cannula 18 may be moved relative to one another such that the suture retention notch 40 may be distally disposed relative to the open distal end 28 of the cannula 18.

Handles, including handle 22, for providing the relative movement described herein are known, and it should be appreciated that the simplified embodiment shown is not intended to limit the scope of the present disclosure. The handle 22 may be configured to bias the suture passer 10 to the retracted position of FIG. 1. For example, an actuable portion 70 of the handle 22 may be attached to the stylet 20 and may be movable, such as axially movable, within another portion 72 of the handle 22 that is attached to the cannula 18. A spring 74 or other similar mechanism may bias the actuable portion 70 such that the suture passer 10 is maintained in the refracted position of FIG. 1. A clinician may then move the actuable portion 70 against the spring force to transition the suture passer 10 from the retracted position of FIG. 1 to the expanded position of FIG. 2. Releasing the actuable portion 70 may permit the spring 74 to return the suture passer 10 to the biased position.

As shown in FIG. 4, a suture passer 80 according to the present disclosure may include a preformed curve 82. The suture passer 80 may be similar to the suture passer 10 described above and may include a handle 84 supporting a cannula 86 and stylet 88. The handle 84 may be configured to move at least one of the cannula 86 and the stylet 88 relative to the other such that the suture passer 80 may be moved between a retracted position and an extended position. The retracted and extended positions may be similar to those described above, wherein the stylet 88 is distally advanced relative to the cannula 86 to expose a suture retention notch as the suture passer 80 is moved from a refracted position to an extended position. According to this embodiment, and others, a control wire 90, shown in FIG. 5, having a polygonal cross-sectional shape may be used. For example, the control wire 90 may be a flat wire having a substantially rectangular cross-sectional shape. According to such an embodiment, the cannula 86 includes the preformed curve 82, with the preformed curve 82 and the control wire 90 occupying a common plane such that advancement of the control wire 90 along the curve 82 is improved.

Turning now to FIGS. 6 and 7, a distal portion of an alternative suture passer 100 according to the present disclosure is shown. The suture passer 100 may be similar to the suture passers 10 and 80 described above, and may generally include a cannula 102 and a stylet 104 movable between an extended position, shown in FIG. 6, and a retracted position, shown in FIG. 7. According to the depicted embodiment, a proximal segment 106 of the stylet 104 may also include a longitudinal key 108 and have an outer diameter $d_3$ substantially matching a cannula outer diameter $d_4$. The longitudinal key 108 is aligned with and received within a longitudinal slot 110 through the cannula 102 as the suture passer 100 is moved between the extended position of FIG. 6 and the retracted position of FIG. 7. As should be appreciated, the longitudinal key 108 and longitudinal slot 110 may assist in rotational alignment of the stylet 104 and the cannula 102.

INDUSTRIAL APPLICABILITY

Turning now to FIG. 8, a procedure using the suture passer 10, described above with reference to FIGS. 1-3, will be discussed. For example, a ventral hernia repair may require the use of the suture passer 10. Although ventral hernia repair procedures may vary, a number of these procedures involve the placement of a soft tissue repair prosthetic 120 across an abdominal wall 122 to cover or repair a defect. According to a specific exemplary procedure, a number of sutures 124 may be provided through the prosthetic 120 and may each include a knotted end 126 and a free end 128. The suture passer 10 may be passed through the abdominal wall 122, which may include skin, fascia, and muscle and may be referred to herein as soft tissue, to capture each free end 128 and pull the suture 124 through or toward the abdominal wall 122.

First, as shown in FIG. 8, the suture passer 10 may be advanced through the soft tissue 122 with the suture passer 10 in the retracted position, also shown in FIG. 1, which defines a continuous outer diameter at a transition 130 between the cannula 18 and the stylet 20. According to the retracted position, as described above, the proximal segment 34 of the stylet 20 is received within the cannula 18 through the open distal end 28 and the shoulder 68 defining the transition between the proximal segment 34 and the distal segment 36, which corresponds to the transition 130 in the retracted position, abuts the open distal end 28 of the cannula 18. The beveled tip 66 and smooth transition 130 may minimize the force required to pass the suture passer 10 through the soft tissue 122. In addition, the utilization of a smooth transition 130 may reduce trauma to the soft tissue 122 that may otherwise occur with a transition that is not smooth.

Figure 9:
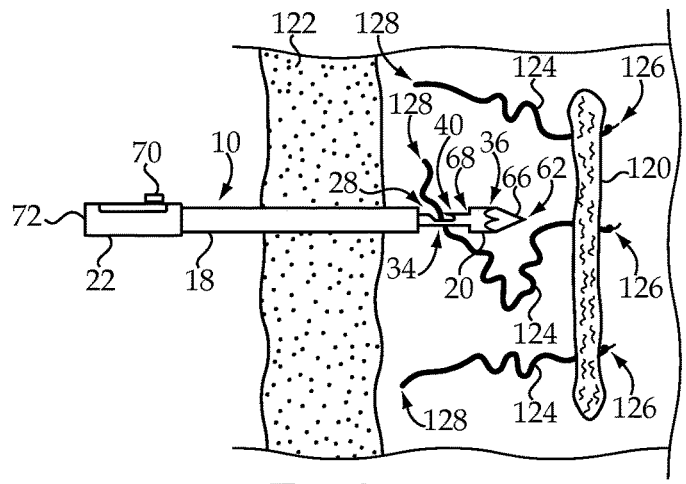
FIG. 9 is a partially sectioned side diagrammatic view at another procedure stage.
Figure 10:
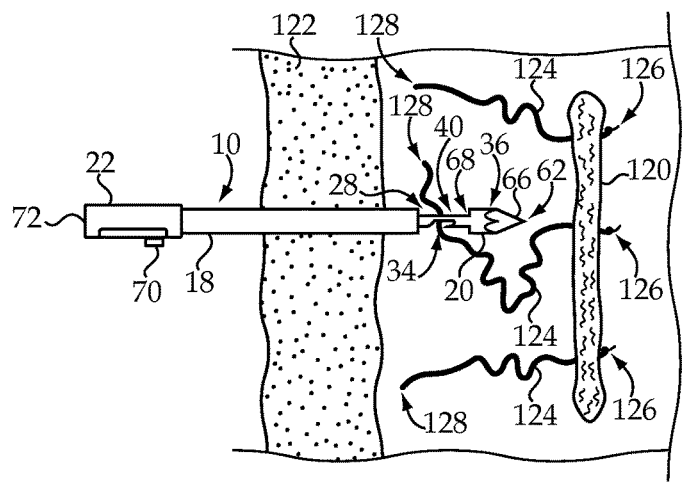
FIG. 10 is a partially sectioned side diagrammatic view at another procedure stage.

Next, as shown in FIG. 9, the suture passer 10 may be moved from the retracted position to the extended position, which is also shown in FIG. 2, in which the suture retention notch 40 is distally disposed relative to the open distal end 28 of the cannula 18. As described above, a clinician may manipulate the handle 22 to move the suture passer 10 from the retracted position to the extended position. In particular, the stylet 20 may be advanced relative to the cannula 18, or the cannula 18 may be retracted relative to the stylet 20, to expose the suture retention notch 40. The suture passer 10 may be repositioned, such as axially or rotationally, to align the suture retention notch 40 with one of the sutures 124 such that the suture 124 is received within the suture retention notch 40, as shown in FIG. 10.

Figure 11:
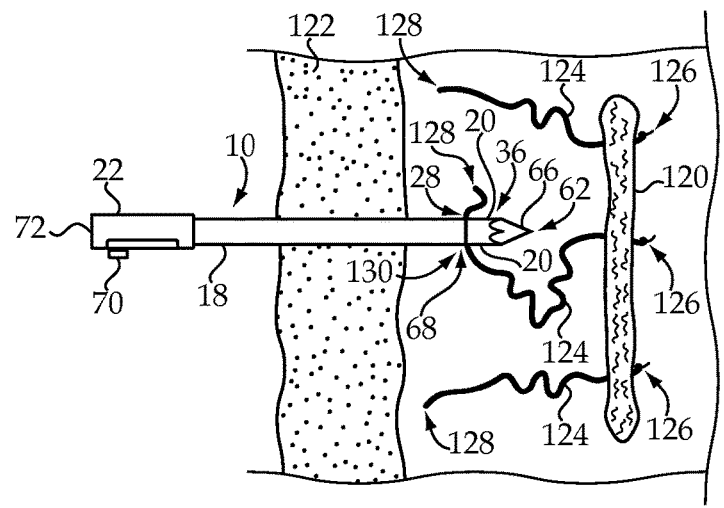
FIG. 11 is a partially sectioned side diagrammatic view at another procedure stage.
Figure 12:
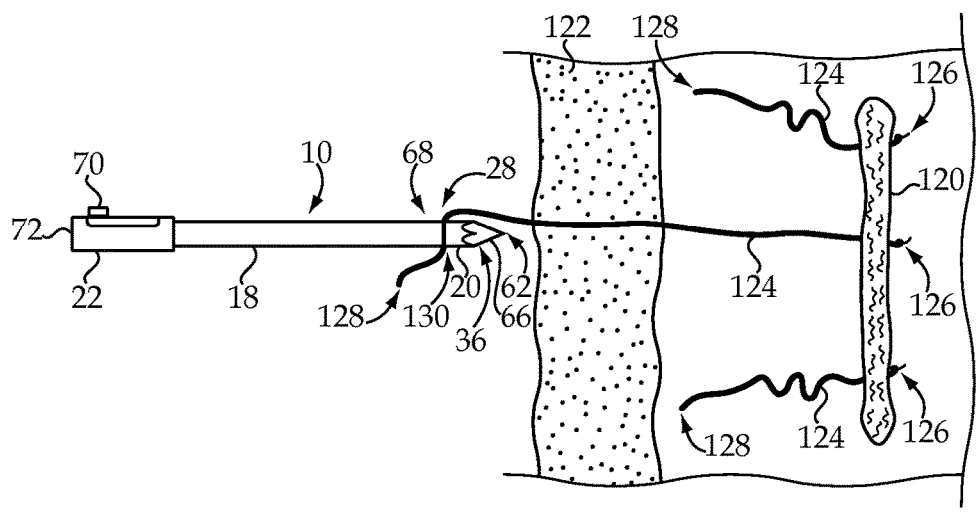
FIG. 12 is a partially sectioned side diagrammatic view at another procedure stage.

Next, the suture 124 may be captured with the suture passer 10 by moving, or returning, the suture passer 10 to the retracted position. Specifically, as shown in FIG. 11, the suture passer 10 is moved from the extended position to the retracted position, with the suture 124 captured in the suture retention notch 40. With the suture passer 10 in the retracted position, the suture passer 10 may be proximally withdrawn back through the soft tissue 122, passing the suture 124 through the soft tissue 122 as well. The described procedure may be repeated until all of the suture free ends 128 are pulled through the soft tissue 122 and tied together, or otherwise secured. Of course, this specific procedure is provided for exemplary purposes only. The suture passer 10 disclosed herein may be used in a variety of alternative procedures requiring suture placement or movement.

The suture passer described herein provides a smooth and efficient means for passing a suture through soft tissue. In particular, the suture passer of the present disclosure includes a continuous outer diameter at a transition between the cannula and the stylet to reduce trauma or damage to the soft tissue and minimize the force required to advance the suture passer through the soft tissue. In addition, the stylet may include a body portion supporting the suture retention notch, with the remaining portion of the stylet including a control wire. The control wire may have a reduced diameter relative to the body portion of the stylet and may improve relative movement of the stylet, particularly within a curved cannula. Rotational alignment features, as taught herein, along with additional enhancements and features may also be provided to improve performance of the suture passer.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A suture passer, comprising:
    a cannula having an open distal end defining a cannula outer diameter; and
    a stylet having a proximal segment configured for receipt within the cannula and including a suture retention notch, and a distal segment having an expanded outer diameter substantially matching the cannula outer diameter, wherein the distal segment terminates at a distal cutting edge;
    wherein the suture passer includes a retracted position in which the proximal segment of the stylet is received within the cannula through the open distal end and a shoulder defining a transition between the proximal segment and the distal segment abuts the open distal end of the cannula, and an extended position in which the suture retention notch is distally disposed relative to the open distal end of the cannula; and wherein the proximal segment of the stylet includes a longitudinal key having an outer diameter substantially matching the cannula outer diameter, wherein, in the retracted position, the longitudinal key is received within a longitudinal slot through the cannula.

2. The suture passer of claim 1, wherein the proximal segment of the stylet spans a majority of a length of the cannula.

3. The suture passer of claim 1, wherein the proximal segment includes a control wire and a proximal length of a body portion.

4. The suture passer of claim 3, wherein the control wire has an ovoid cross-sectional shape.

5. The suture passer of claim 3, wherein the control wire has a polygonal cross-sectional shape.

6. The suture passer of claim 5, wherein the cannula includes a preformed curve, wherein the preformed curve and the control wire occupy a common plane.

7. The suture passer of claim 1, wherein the cannula includes a preformed curve.

8. The suture passer of claim 1, wherein the stylet is solid.

9. The suture passer of claim 1, wherein the cannula has a blunt distal tip.

10. The suture passer of claim 1, wherein the distal segment of the stylet terminates at a tip having a multitude of bevels.

11. The suture passer of claim 1, further including a handle disposed at a proximal end of the suture passer and configured to move the suture passer between the retracted and extended positions.

12. The suture passer of claim 11, wherein the suture passer is biased to the retracted position.

13. A method of operating a suture passer, the suture passer including: a cannula having an open distal end defining a cannula outer diameter; and a stylet having a proximal segment configured for receipt within the cannula and including a suture retention notch, and a distal segment having an expanded outer diameter substantially matching the cannula outer diameter, wherein the distal segment terminates at a distal cutting edge, and wherein the suture passer includes a retracted position in which the proximal segment of the stylet is received within the cannula through the open distal end and a shoulder defining a transition between the proximal segment and the distal segment abuts the open distal end of the cannula, and an extended position in which the suture retention notch is distally disposed relative to the open distal end of the cannula, and wherein the proximal segment of the stylet includes a longitudinal key having an outer diameter substantially matching the cannula outer diameter, wherein, in the retracted position, the longitudinal key is received within a longitudinal slot through the cannula, the method comprising steps of:

advancing the suture passer through soft tissue with the suture passer in the retracted position defining a continuous outer diameter between the cannula and the stylet;

moving the suture passer from the retracted position to the extended position in which the suture retention notch is distally disposed relative to the open distal end of the cannula;

receiving a suture within the suture retention notch of the stylet; and capturing the suture with the suture passer by returning the suture passer to the retracted position.

14. The method of claim 13, further including moving the suture passer between the retracted and extended positions using a handle disposed at a proximal end of the suture passer.

15. The method of claim 14, further including biasing the suture passer to the retracted position.

16. The method of claim 14, wherein moving the suture passer between the retracted and extended positions includes sliding the longitudinal key of the proximal segment of the stylet within the longitudinal slot through the cannula.

17. The method of claim 13, further including moving the stylet along a preformed curve of the cannula.

18. The method of claim 13, further including moving a control wire along a preformed curve of the cannula, wherein the control wire is received through the cannula and has a distal end attached to the proximal segment of the stylet.

19. The method of claim 13, wherein the advancing step includes piercing the soft tissue with a tip of the stylet, wherein the tip has a multitude of bevels.

* * * * *